United States Patent

Sawyers et al.

Patent Number: 5,310,686
Date of Patent: May 10, 1994

[54] POLYMER-COATED OPTICAL STRUCTURES

[75] Inventors: Craig G. Sawyers, Cambridgeshire; Rosemary A. L. Drake, Hertfordshire, both of England

[73] Assignee: Ares Serono Research & Development Limited partnership, Switzerland

[21] Appl. No.: 270,339

[22] PCT Filed: Mar. 9, 1988

[86] PCT No.: PCT/GB88/00177
§ 371 Date: Nov. 4, 1988
§ 102(e) Date: Nov. 4, 1988

[87] PCT Pub. No.: WO88/07203
PCT Pub. Date: Sep. 22, 1988

[30] Foreign Application Priority Data

Mar. 10, 1987 [GB] United Kingdom ............... 8705649

[51] Int. Cl.⁵ ............... G01N 33/543; G01N 33/553; G01N 33/551
[52] U.S. Cl. .................. 436/518; 436/524; 436/525; 436/531; 436/164; 436/805
[58] Field of Search ............... 436/517, 524, 531, 164, 436/805; 369/46; 435/4, 7, 808; 424/421, 436, 496, 492; 427/2

[56] References Cited

U.S. PATENT DOCUMENTS

| | | |
|---|---|---|
| 3,932,184 | 1/1976 | Cohen et al. .............. 430/321 |
| 4,647,544 | 3/1987 | Nicoli et al. .............. 436/518 |
| 4,674,020 | 6/1987 | Tajima et al. .............. 369/46 |
| 4,876,208 | 10/1989 | Gustafson et al. .......... 436/531 |

FOREIGN PATENT DOCUMENTS

| | | |
|---|---|---|
| 142810 | 5/1985 | European Pat. Off. |
| 171148 | 2/1986 | European Pat. Off. |
| 254575 | 1/1988 | European Pat. Off. |
| WO84/02578 | 7/1984 | PCT Int'l Appl. |
| WO86/01901 | 3/1986 | PCT Int'l Appl. |

Primary Examiner—Toni R. Scheiner
Attorney, Agent, or Firm—Osterlenk, Faber, Gerb & Soffen

[57] ABSTRACT

A method is disclosed for coating the surface of an optical structure, such as a diffraction grating, useful for the detection of a ligand, which method comprises forming on the surface of the optical structure a thin, uniform layer of a polymerizable material, particularly one which polymerizes on exposure to light or heat, and subsequently exposing said material to polymerizing conditions. A specific binding partner is subsequently absorbed on or bound to the cured polymer layer, either directly or indirectly. Complex formation between the specific binding partner and ligand present in the sample to be analyzed alters the optical properties of the device and the change forms the basis of an assay.

9 Claims, No Drawings

POLYMER-COATED OPTICAL STRUCTURES

The present invention relates to methods of producing polymer-coated surfaces suitable for use as optical structures. In particular it relates to methods of producing surfaces suitable for use in sensors, for example in biosensors in which one of a pair of binding partners is applied to the surface of a polymer-coated optical structure to form a device for detecting the presence of the complementary component in a sample subsequently brought into contact with the surface.

The properties of simple optical structures have been known for many years and structures such as, for example, diffraction gratings have widespread use, not only as tools for understanding and analysing the wave properties of electromaqnetic radiation but also, more recently, as sensors for detecting chemical, biochemical or biological species in a sample.

U.S. Pat. Nos. 3926564 and 3979184 both describe the adsorption of immunologically reactive proteins onto rough metallic surfaces such that binding of a complementary component changes the optical properties of the surface in a manner detectable by the unaided eye.

EP-0112721 describes the preparation, and use as biosensors, of metallised diffraction gratings coated with a material (hereinafter called "specific binding partner") capable of binding with the species to be assayed (hereinafter called "specific binding partner") capable of binding with the species to be assayed (hereinafter called "ligand") to form a complex. The optical properties of such diffraction gratings are altered as a result of complex formation between the specific binding partner and the ligand and this phenomenon can consequently form the basis of an assay system.

A problem common not only to the use of coated optical structures as biosensors but also to the use of standard optical structures by experimental physicists, is the difficulty of controlling their surface properties. The supporting substrate of such optical structures is often of glass or plastics material but the surface of the structure, particularly where a surface plasmon resonance effect is desired, may comprise a thin metal layer formed, for example, by vacuum deposition. Problems can arise with the use of metal-coated surfaces in corrosive environments which may destroy the integrity of a metal layer. Other inorganic layers e.g. silicon oxide have also been described as diffraction grating surfaces (see, for example, EP-0112721 and EP-0178083). However, it has been observed that silicon oxide does not provide complete protection against chemical attack, particularly if a silver layer is to be protected from attack by saline solutions. The extent of the attack will depend on the thickness of the protective layer and the length of time of exposure to corrosive chemicals. For maximum assay sensitivity an appropriate uniform coating thickness must be provided in the range 10–200 nm. If the sensor is exposed to saline solutions for extended periods of time then it appears that ions can penetrate through the oxide or other layer to produce a tarnish on the silver which may eventually result in the removal of the protective layer thus reducing the usefulness of the device.

Certain of the optical properties of an optical structure, for example its reflection and/or transmission properties and any surface plasmon resonance effect exhibited, will depend on the composition, thickness and uniformity of any surface layers present; the composition of any such surface layers also governs the chemical properties of the optical structure. However, the range of chemical and physical properties of known inorganic layers is limited. A still further problem which may occur when using such optical structures as biosensors is that some biologically active materials, e.g. proteins, may be at least partially inactivated by direct contact with metallic and certain inorganic surfaces.

In contrast, an extremely wide range of chemical and physical properties can be achieved by using appropriate organic polymers and a large number of techniques are known for bonding thereto or adsorbing thereon chemical, biochemical and biological entities. Unfortunately, previous attempts to prepare polymer-coated diffraction gratings have resulted in the polymer coating failing to conform adequately to the surface relief profile of the grating thereby grossly distorting its inherent physical properties.

We have now found that by using a material which is capable of cross-polymerising on exposure to light or to heat it is possible to prepare an optical structure having a uniformly distributed surface layer of organic polymer which conforms well to the surface relief profile of the optical structure. This layer provides an appropriate surface to resist chemical attack, and thus to protect any underlying metal layer, and for the optional attachment of a specific binding partner thereto.

Thus, in its broadest aspect, the invention provides a method of treating the surface of an optical structure which comprises forming on said surface a thin layer of a material which is capable of cross-polymerising on exposure to light or to heat. Subsequently the said material may be exposed to light or to heat whereby polymerisation occurs.

In general, the layer of polymerised material on the surface of the optical structures will have a thickness in the range 10 to 200 nanometers.

The material used may be any suitable material which is capable of forming a thin uniform layer which cross-polymerises on exposure to light or to heat. Suitable materials include thermo-polymerisable materials such as polyimide and photo-polymerisable materials such as photoresists e.g. positive, negative and electron ($e^-$) beam photoresists. Preferably the material is a negative photoresist material such as is used extensively in semiconductor fabrication and microlithography. Such photoresist materials are designed to withstand chemical attack and have been found to not only protect the underlying surface against such attack but also to protect it against ion penetration. Negative photoresists are typically cyclized polyisoprene based, for example cyclised cis-1,4 polyisoprene. Such material may be applied in a thin uniform layer to the surface of an optical structure in a convenient, well-controlled manner which lends itself to volume manufacture.

As mentioned previously the optical characteristics of an optical surface depend not only on its physical relief profile but also on the composition of the surface layer or layers. Thus, the process of the present invention can be applied to produce novel coated optical structures which may prove to be useful tools for experimental physicists and the like. In addition, certain preferred surface layers such as, for example, those capable of supporting surface plasmon resonance e.g. silver may be particularly susceptible to corrosion by, for example, aqueous environments; the present invention provides a means of passivating such a layer such that its integrity is maintained under practical working conditions.

However, the present invention is of particular advantage where the optical structures are diffraction gratings intended to be used as biosensors in a manner analogous to previous proposals (see, for example, EP-0112721). Direct contact between a biologically active material, such as, for example, an antibody or antigen, and a metallic surface may result in contamination or destruction of its biological activity. In this situation the polymer layer conveniently acts as a barrier. Furthermore, the wide range of chemical properties of different polymer surfaces (e.g. availability of free groups for covalent bonding, hydrophilicity or hydrophobicity, surface charge and dielectric properties) provide versatility and scope for optimising the binding or adsorption of any particular binding partner, such as, for example, an antibody or an antigen. It is important to maintain the native conformation and biological activity of the desired binding partner and to obtain satisfactory immobilisation onto the surface of the optical structure whilst minimising any non-specific binding or steric hindrance.

The method of the present invention hence has particular use in the preparation of biosensors and thus according to one embodiment of the present invention there is provided a method of preparing a device for the detection of a ligand which comprises:

a) forming on the surface of an optical structure a thin layer of a material which is capable of cross-polymerising on exposure to light;
b) exposing said material to light whereby polymerisation occurs; and
c) adsorbing on or binding to said polymerised material, either directly or indirectly, a specific binding partner for the ligand it is desired to detect.

Biosensors produced in accordance with the invention are especially useful for the detection of antibodies or antigens (in which case the specific binding partner may be an antigen or an antibody, monoclonal or polyclonal, respectively) but other ligands may be detected by the use of other specific binding partners, as discussed hereinafter. However, the sensors produced in accordance with the invention are not limited to biosensors and may comprise chemical sensors such as, for example, gaseous chemical detectors wherein specific adsorption onto or absorption into the polymer layer may occur.

The optical properties of an optical structure coated with a specific binding partner are altered by complex formation between the specific binding partner and the complementary ligand and, in one embodiment of the invention, by comparing the optical characteristics of a standard (untreated) region with those of a treated test region of the surface it is possible to determine qualitatively or quantitatively whether a binding reaction has occurred in the test region. In an alternative embodiment where, for example, the specific binding partner is an antibody, an antibody specific to the antigen to be tested for is adsorbed on or bound to at least one discrete test region on the surface of an optical structure and a protein which is not a specific binding partner for any ligand which may be present in the sample to be tested (denoted herein as a "non-specific protein") is adsorbed on or bound to at least one discrete reference region on said surface. The non-specific protein may be, for example, an inactivated antibody or an antibody raised against a ligand not present in the samples to be tested e.g. where the samples to be tested are human sera, the non-specific protein may be an anti-mouse antibody. Any differences between the non-specific binding of e.g. proteins present in the test sample to either the specific antibody or the non-specific protein can be determined by comparing the optical properties of the test region with the reference region after exposure to a sample which does not contain the antigen to be tested for, so that an appropriate correction can, if necessary, be made. Comparison of the optical characteristics of the test and standard regions of a similar biosensor during or after exposure to a sample to be tested can then provide a measurement of complex formation between the antigen to be tested for and its specific antibody. Each region may comprise a continuous layer of a specific binding partner or each binding partner may be present at discrete intervals within any given region to form a discontinuous layer.

The biosensors produced in accordance with the invention may, for example, be used in assays in ways analogous to those described in EP-0112721 and EP-0178083.

Techniques for bonding specific binding partners to solid phase supports are described in the literature. The binding partner may be bound to the polymer either directly or indirectly. Indirect binding may, for example, be effected by binding to the polymer a reagent Y which selectively interacts with a reagent Z provided on the specific binding partner. In such cases, the reagent Z may for example be such as to render the specific binding partner antigenic to reagent Y which in that case will be an antibody raised to Z. Z may for example be fluorescein isothiocyanate, rhodamine isothiocyanate, 2,4-dinitrofluorobenzene, phenyl isothiocyanate or dansyl chloride. Reagents Y and Z may alternatively be a specific binding protein and the corresponding ligand such as for example avidin and biotin.

It is a desirable but not an essential feature of the invention to provide covalent bonding of the binding partner to the polymer.

The bonding of the specific binding partner, either directly or indirectly, to the polymer may be facilitated by activating the polymer layer, to provide free reactive groups for bonding. Thus, for example an organo functional silane layer such as aminopropyltriethoxysilane may be applied followed by treatment with glutaraldehyde. This provides aldehyde groups on the surface of the optical structure which may covalently couple to amino groups present on proteins, or other entities comprising the specific binding partner.

Thus according to a further aspect of the invention there is provided a biosensor for detecting a ligand comprising an optical structure bearing a thin layer of a material which has been cross-polymerised by exposure to light or to heat, the said material having adsorbed thereon or bound thereto, either directly or indirectly, a specific binding partner for the ligand it is desired to detect.

The present invention further provides a method of detecting a ligand in a sample which comprises contacting said sample with a biosensor as described herein and determining whether, and if desired the extent to which and/or rate at which, an optical characteristic of the biosensor is altered by formation of a complex between the ligand and the specific binding partner.

The invention will be particularly described hereinafter with reference to an antibody or an antigen as the specific binding partner or ligand. However, the invention is not to be taken as being limited to methods of preparing biosensors suitable for use in antibody or antigen assays but includes within its scope any sensors prepared by the process of the invention which can be used to detect any chemical, biochemical or biological species in a sample. Examples of suitable binding partners which may be immobilised on an optical structure prepared by the process of the invention and of ligands which may be assayed by the method of the invention are given in Table I below.

TABLE I

| Ligand | Specific Binding Partner |
|---|---|
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to provide biosensors suitable for assaying: hormones, including peptide hormones (e.g. thyroid stimulating hormone (TSH), luteinising hormone (LH), human chorionic gonadotrophin (hCG), follicle stimulating hormone (FSH), insulin and prolactin) and non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxins, vitamins, viruses, bacteria or microorganisms.

It will be understood that the term "antibody" used herein includes within its scope
 a) any of the various classes or sub-classes of immunoglobulin, e.g. IgG, IgM, derived from any of the animals conventionally used, e.g. sheep, rabbits, goats or mice,
 b) monoclonal antibodies,
 c) intact molecules or "fragments" of antibodies, monoclonal or polyclonal, the fragments being those which contain the binding region of the antibody, i.e. fragments devoid of the Fc portion (e.g., Fab, Fab', F(ab')2) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacteria fragments, cells, cell fragments and viruses) and haptens which may be rendered antigenic under suitable conditions.

The invention will be described in more detail with reference to a preferred embodiment wherein the optical structure is a diffraction grating. However, it is to be understood that other optical structures such as, for example, optical waveguides, optical fibres and metal-coated prisms in the correct configuration to exhibit surface plasmon resonance, are all included within the scope of the invention.

As previously mentioned, the supporting substrate of a diffraction grating may comprise glass or plastics material; polycarbonate is particularly preferred. The diffraction grating may be formed in the surface of the supporting substrate which may be covered with, for example, a metal film, such as silver, gold, copper, nickel or aluminium, formed by a process of vapour deposition, electroplating, sputtering, coating, painting, spraying or otherwise. Preferably the metal surface is capable of supporting surface plasmon resonance, and more particularly is of silver, and the metallic film is deposited by vacuum deposition.

Where the diffraction grating is to be used in an optical transmission mode, the metal film must be sufficiently thin, for example up to 50 nm for silver, so as not to unduly impede the passage of light therethrough. Where the diffraction grating is to be used in a reflective mode, then the metal layer can be thicker, for example up to 500 nm, preferably around 100 nm for silver, and is preferably made sufficiently dense to provide a good reflecting surface on the diffraction grating pattern in the surface of the supporting substrate e.g. of plastics or glass.

A preferred method of applying a thin layer of a material which is capable of cross-polymerising on exposure to light, preferably a photoresist, to the surface of a metallised diffraction grating comprises the steps of:
 i) locating the diffraction grating, with the optical surface uppermost, on a spinner;
 ii) securing the diffraction grating to the spinner, preferably by means of a vacuum applied between the spinner and the diffraction grating;
 iii) applying a metered volume of a negative photoresist material or a solution of the negative photoresist material in a suitable solvent, for example in a mixture of xylene isomers to the surface of the diffraction grating;
 iv) spinning the diffraction grating secured to the spinner, for example at several thousand r.p.m. for a period of e.g. 30 seconds, such that the negative photoresist material or the solution thereof is distributed as a thin uniform layer over the surface of the diffraction grating;
 v) if required, heating the diffraction grating such that any solvent remaining in the negative photoresist layer evaporates; and
 vi) exposing the negative photoresist layer to light such that polymerisation, preferably polymerisation of substantially all reactive groups in the negative photoresist material, occurs.

Subsequently, if desired, the negative photoresist layer may be exposed, either directly or indirectly, to a solution containing a specific binding partner e.g. an antibody or an antigen such that adsorption or binding of the specific binding partner to the surface of the negative photoresist material occurs.

Where a sheet of diffraction grating has an area greater than that required the sheet can be cut up into suitably sized parts.

It will be appreciated that where a solution of photoresist material is used the solvent must be compatible with the surface material of the diffraction grating and must be readily removable by evaporation, for example by heating the coated diffraction grating in an oven at a temperature of e.g. 80°-120° C. for a period of e.g. 10°-60 minutes (using fume extraction equipment where appropriate).

BINDING OF BIOLOGICAL MATERIALS TO THE POLYMER SURFACE

Three different methods of coupling biological materials to a polymer surface on a diffraction grating, have been considered:
(a) covalent bonding
b) non-covalent adsorption
c) covalent bonding of the biological material to a second polymer which is entrapped within the first polymer.

a) Covalent Bonding

Established procedures exist for covalently bonding biological materials, such as proteins, to polymers. Published procedures include the use of chemical reagents which modify the polymer unit to form reactive groups which covalently bind to typical protein groups such as, for example, free amino groups.

Commonly used chemical reagents include:
cyanogen bromide
tosyl chloride
titanium complexes
carbodiimide
cyanuric chloride
oxirane
periodate.

Alternatively, a further material may be applied to the negative photoresist layer to provide appropriate bonding groups for subsequent covalent coupling. Thus, for example, the negative photoresist layer may be exposed to an organo functional silane such as aminopropyltriethoxysilane in a suitable solvent e.g. in aqueous solution and, after removing excess silane, any suitable activating agent e.g. glutaraldehyde can be added thereto. Subsequently any excess can be removed before exposing the activated surface of the diffraction grating to a specific binding partner for the ligand it is desired to detect.

b) Non-Covalent Adsorption

Biological materials, for example, sheep serum proteins, ribonucleases and immunoglobulins, have been found to bind very efficiently to some polymers. Simple addition of an aqueous protein solution at room temperature or lower has resulted in bound protein which could not easily be removed by washing with water, buffer solutions or detergents.

c) Reactive Polymer Entrapment

This procedure separates the two important functions of the diffraction grating layer
adhesion and conformation to the grating surface
reactivity towards protein or other biological material or binding partner and meets each requirement with a separate polymer.

A monomeric material is allowed to diffuse into the light-induced polymer affixed to the diffraction grating. The monomer is then polymerised to give a network of the second polymer entangled in the first, affixed polymer. The second polymer is chosen to have chemical groups that are reactive towards protein or other biological materials.

Where a sensor (either before or after the adsorbtion thereon or binding thereto of a specific binding partner e.g. an antibody) is to be stored for a period of time, a further protective barrier coating may be applied to protect the coatings so far applied or, if appropriate, the coated substrate may be freeze-dried or simply dried to allow the sensor to be stored dry.

A preferred method of applying a thin layer of a material which is capable of cross-polymerising on exposure to heat, preferably polyimide, onto a glass surface comprises the steps of:
1) washing glass surface for 60 minutes in a deionised water weir;
2) washing in 10% Decon 90 Ultrasonic tank for 7 minutes;
3) wash with de-ionised water;
4) spin dry in FSI rinser drier;
5) dry for 3 hours at 100° C;
6) treat surface with standard silane coupling reagent;
7) spin on standard polyimide e.g. NOLIMID 32;
8) conveyor baking at approximately 130° C. for 5 minutes; and
9) final bake for 1 hour at 200° C.

We claim:
1. A method of preparing a diffraction grating useful for the detection of a ligand comprising
   (a) applying a metered volume of a polymerizable material to the surface of said diffraction grating and spinning said diffraction grating to distribute said polymerizable material as a thin, uniform layer over the surface thereof;
   (b) polymerizing said material; and
   (c) adsorbing on or binding to said polymerized material, either directly or indirectly, a specific binding partner for said ligand.
2. A method according to claim 1 wherein said diffraction grating is a metallized diffraction grating.
3. A method according to claim 2 wherein said diffraction grating is capable of exhibiting surface plasmon resonance.
4. A method according to claim 1 wherein said specific binding partner is an antigen or an antibody.
5. A method according to claim 1 wherein said polymerizable material comprises a negative photoresist and said polymerizing is conducted by exposing said material to light.
6. A method according to claim 5 wherein said negative photoresist comprises cyclized cis-1,4-polyisoprene.
7. A method according to claim 3 wherein said polymerizable material comprises a negative photoresist and said polymerizing is conducted by exposing said material to light.
8. A method according to claim 7 wherein said negative photoresist comprises cyclized cis-1,4-polyisoprene.
9. A method according to claim 1 wherein said polymerized material is to 200 nanometers thick.

* * * * *